United States Patent
Sato et al.

(10) Patent No.: US 9,820,484 B2
(45) Date of Patent: Nov. 21, 2017

(54) DIHOMO-γ-LINOLENIC ACID-CONTAINING MICROBIAL OIL AND DIHOMO-γ-LINOLENIC ACID-CONTAINING MICROBIAL BIOMASS

(71) Applicant: NIPPON SUISAN KAISHA, LTD., Tokyo (JP)

(72) Inventors: Seizo Sato, Tokyo (JP); Takuro Fukae, Tokyo (JP); Naomi Ohtsuka, Tokyo (JP); Hideaki Yamaguchi, Tokyo (JP); Rie Ikeda, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

(21) Appl. No.: 15/101,581

(22) PCT Filed: Dec. 4, 2014

(86) PCT No.: PCT/JP2014/082770
§ 371 (c)(1),
(2) Date: Jun. 3, 2016

(87) PCT Pub. No.: WO2015/083843
PCT Pub. Date: Jun. 11, 2015

(65) Prior Publication Data
US 2017/0000116 A1 Jan. 5, 2017

(30) Foreign Application Priority Data
Dec. 4, 2013 (JP) ................. 2013-251401

(51) Int. Cl.
| | |
|---|---|
| *A01N 37/06* | (2006.01) |
| *A61K 8/99* | (2017.01) |
| *A61K 31/202* | (2006.01) |
| *C11B 1/02* | (2006.01) |
| *C11B 3/12* | (2006.01) |
| *C11C 1/00* | (2006.01) |
| *A61K 8/36* | (2006.01) |
| *A61Q 19/00* | (2006.01) |
| *C12N 1/28* | (2006.01) |
| *C12P 7/64* | (2006.01) |
| *A23D 9/013* | (2006.01) |
| *A23D 9/02* | (2006.01) |
| *C11B 3/10* | (2006.01) |
| *C11C 3/10* | (2006.01) |
| *A23K 20/158* | (2016.01) |
| *A23L 33/115* | (2016.01) |
| *A61K 36/06* | (2006.01) |

(52) U.S. Cl.
CPC ............ *A01N 37/06* (2013.01); *A23D 9/013* (2013.01); *A23D 9/02* (2013.01); *A23K 20/158* (2016.05); *A23L 33/115* (2016.08); *A61K 8/361* (2013.01); *A61K 8/99* (2013.01); *A61K 31/202* (2013.01); *A61K 36/06* (2013.01); *A61Q 19/00* (2013.01); *C11B 1/025* (2013.01); *C11B 3/10* (2013.01); *C11B 3/12* (2013.01); *C11C 1/005* (2013.01); *C11C 3/10* (2013.01); *C12N 1/28* (2013.01); *C12P 7/6427* (2013.01); *C12P 7/6436* (2013.01); *C12P 7/6463* (2013.01)

(58) Field of Classification Search
CPC ...................................................... A61K 36/00
See application file for complete search history.

(56) References Cited

U.S. PATENT DOCUMENTS

| | | | |
|---|---|---|---|
| 4,776,984 | A | 10/1988 | Traitler et al. |
| 5,145,686 | A | 9/1992 | Horrobin et al. |
| 5,668,174 | A | 9/1997 | Kawagishi et al. |
| 5,847,000 | A | 12/1998 | Horrobin et al. |
| 5,914,347 | A | 6/1999 | Grinda |
| 5,968,809 | A * | 10/1999 | Knutzon ............... A23D 9/00 435/189 |
| 5,972,664 | A | 10/1999 | Knutzon et al. |
| 6,177,470 | B1 | 1/2001 | Horrobin et al. |
| 2001/0021522 | A1 | 9/2001 | Kawashima et al. |
| 2003/0166723 | A1 | 9/2003 | Nakajima et al. |
| 2005/0287651 | A1 | 12/2005 | Akimoto et al. |
| 2006/0110806 | A1 | 5/2006 | Damude et al. |

(Continued)

FOREIGN PATENT DOCUMENTS

| | | |
|---|---|---|
| DE | 20 2008 006 708 U1 | 9/2008 |
| EP | 0 085 579 A2 | 8/1983 |

(Continued)

OTHER PUBLICATIONS

International Preliminary Report on Patentability (including PCT/ISA/237) dated Jun. 7, 2016 for PCT/JP2014/082770.

(Continued)

*Primary Examiner* — Qiuwen Mi
(74) *Attorney, Agent, or Firm* — Drinker Biddle & Reath LLP

(57) ABSTRACT

A microbial oil comprising dihomo-γ-linolenic acid as a constituent fatty acid of an oil, the microbial oil has a content, in terms of a weight ratio of arachidonic acid relative to dihomo-γ-linolenic acid (arachidonic acid/dihomo-γ-linolenic acid) of less than 1/13. Preferably, the microbial oil has a triglyceride content of greater than or equal to 70% by weight, and a saturated fatty acid content of less than or equal to 40% by weight. Moreover, a lower alcohol ester of dihomo-γ-linolenic acid or a free fatty acid of dihomo-γ-linolenic acid obtained from the microbial oil is provided.

20 Claims, No Drawings

(56) References Cited

U.S. PATENT DOCUMENTS

| | | |
|---|---|---|
| 2008/0108699 A1 | 5/2008 | Tateishi et al. |
| 2010/0317622 A1 | 12/2010 | Kawashima et al. |
| 2011/0263708 A1 | 10/2011 | Cohen et al. |
| 2012/0142773 A1 | 6/2012 | Kelliher et al. |
| 2016/0051504 A1 | 2/2016 | Takeo et al. |

FOREIGN PATENT DOCUMENTS

| | | |
|---|---|---|
| EP | 0 173 478 A1 | 3/1986 |
| EP | 0 454 102 A2 | 10/1991 |
| EP | 0 611 569 A1 | 8/1994 |
| EP | 0 675 120 A2 | 10/1995 |
| GB | 2 327 347 A | 1/1999 |
| JP | S58-208217 A | 12/1983 |
| JP | H05-91887 A | 4/1993 |
| JP | H07-233062 A | 9/1995 |
| JP | H10-218731 A | 8/1998 |
| JP | H10-508287 A | 8/1998 |
| JP | 2002-047176 A | 2/2002 |
| JP | 3354581 B2 | 12/2002 |
| JP | 2006-219454 A | 8/2006 |
| WO | WO-2005/083101 A1 | 9/2005 |
| WO | WO-2006/085687 A1 | 8/2006 |
| WO | WO-2010/125340 A1 | 11/2010 |

OTHER PUBLICATIONS

A. Anstey, et al, "Topical evening primrose oil as treatment for atopic eczema," Journal of Dermatological Treatment (1990) 1, pp. 199-201.

N.L. Morse, et al., "A Meta-Analysis of Randomized, Placebo-Controlled Clinical Trials of Efamol® Evening Primrose Oil in Atopic Eczema. Where Do We Go from Here in Light of More Recent Discoveries?," Current Pharmaceutical Biotechnology, 2006, 7, pp. 503-524.

Extended European Search Report corresponding to Application No. 12781963.9-1460/2708230 PCT/JP2012062114; dated Nov. 4, 2014.

International Search Report for International Application No. PCT/JP2012/062114; dated Jun. 12, 2012, with English Translation.

U.S. Non Final Office Action corresponding to U.S. Appl. No. 14/117,330 (YUA0026US), dated Mar. 6, 2015.

Mark G. Obukowicz, et al., "Novel, Selective Δ6 or Δ5 Fatty Acid Desaturase Inhibitors as Antiinflammatory Agents in Mice," J. Pharm Exp. Ther., vol. 287, No. 1 (1998) pp. 157-166.

International Search Report dated Jul. 10, 2015 for PCT/JP2014/082770.

Written Opinion dated Jul. 10, 2015 for PCT/JP2014/082770.

EP Application No. 14828057.1—Office Action dated Jan. 24, 2017.

Iskandarov, et al., "Selection of DGLA-producing mutant of the microalga Parietochloris incisa: I. Identification of mutation site and expression of VLC-PUFA biosynthesis genes", Appl Microbiol Biotechnol (2011) 90: 249-256.

Office Action dated Aug. 17, 2017 in corresponding EP Application No. 14828057.1.

Kawashima H et al: "Industrial production of dihomo-gamma-linolenic acid by a DELTA5 desaturase-defective mutant of Mortierella alpina 1S-4 fungus", Journal of the American Oil Chemists' Society (JA, Springer, DE, vol. 77, No. 11, Nov. 1, 2000 (Nov. 1, 2000), pp. 1135-1138, XP008084822. ISSN: 0003-021X, DOI: 10.1007/S11746-000-0178-2.

* cited by examiner

DIHOMO-γ-LINOLENIC ACID-CONTAINING MICROBIAL OIL AND DIHOMO-γ-LINOLENIC ACID-CONTAINING MICROBIAL BIOMASS

CROSS-REFERENCE TO REALTED APPLICATIONS

This application is the National Stage of International Application No. PCT/JP2014/082770, filed Dec. 4, 2014, and claims benefit of Japanese Application No. 2013-251401 filed on Dec. 4, 2013.

TECHNICAL FIELD

The present invention relates to a microbial oil containing dihomo-γ-linolenic acid (also referred to hereinafter as DGLA), a dihomo-γ-linolenic acid-containing microbial biomass, and to methods of preparation and uses thereof.

BACKGROUND ART

DGLA (8,11,14-eicosatrienoic acid) is one of the constituent fatty acids in fish oils, marine algae and the like. DGLA is known to be produced as a precursor for arachidonic acid (also referred to hereinafter as ARA) in microbes such as *Mortierella alpina*. However, there is only a slight amount of generation of DGLA in microbes containing triglycerides, diglycerides, monoglycerides, phospholipids and sterols as lipid components. DGLA and ARA are fatty acids that have similar chemical characteristics. Thus, separation of DGLA from ARA is difficult.

Technology has been proposed for decreasing the generated amount of ARA in the microbe in order to produce DGLA in an efficient manner.

For example, Japanese Patent Application Laid-Open (JP-A) No. H5-091887 discloses a method of producing DGLA or a lipid containing DGLA, the method comprising culturing a microbe having an ability to produce arachidonic acid but having a reduced or lost Δ5 desaturation activity, to produce DGLA or DGLA-containing lipids, and recovering the DGLA or DGLA-containing lipids. JP-A No. H-091887 also discloses that the microbe having an ability to produce arachidonic acid and having a reduced or lost Δ5 desaturation activity is cultured in the presence of a Δ5 desaturase inhibitor, e.g. sesamin or the like.

Moreover, WO 2005/083101 discloses a method of producing phospholipid containing a long-chain polyunsaturated fatty acid such as arachidonic acid and DGLA as a constituent component. The method comprises steps of extracting phospholipids from defatted cells obtained by extracting oils/fats containing triglycerides from cells of a lipid-producing microbe, which microbe produces a lipid containing a long-chain polyunsaturated fatty acid as a constituent component.

Despite these prior disclosures, commercial production of DGLA-rich microbial oil has scarcely taken place up to now, because of the technical difficulties in achieving a product of satisfactory and useful quality.

SUMMARY OF THE INVENTION

Problems to be Solved by the Invention

There is increased demand for DGLA-containing oils in higher purity, and the aforementioned technologies have been insufficient for such demand.

An object of the present invention is to provide microbial oil and a microbial biomass capable of use in order to efficiently obtain a dihomo-γ-linolenic acid-containing oil that has a lower arachidonic acid content than that of the oil obtained by conventional method, and to provide corresponding methods of preparation and use thereof.

Means for Solving the Problems

The present invention provides the following.

A first aspect is a microbial oil comprising dihomo-γ-linolenic acid as a constituent fatty acid of the oil, the microbial oil having a weight ratio of arachidonic acid relative to dihomo-γ-linolenic acid (arachidonic acid/dihomo-γ-linolenic acid) of less than 1/13.

The weight ratio of arachidonic acid/dihomo-γ-linolenic acid may be less than or equal to 1/15, preferably less than or equal to 1/20.

Desirably the microbial oil has a triglyceride content of greater than or equal to 70% by weight, more preferably greater than or equal to 90% by weight. It may contain phospholipid e.g. at from 0.1% to 10% by weight.

The content of saturated fatty acid in the oil is desirably not more than 40% by weight.

The microbial oil may be a crude or refined oil. In the crude oil, preferably the triglyceride content is greater than or equal to 90% by weight. The weight ratio of arachidonic acid relative to dihomo-γ-linolenic acid is desirably less than or equal to 1/15 in the crude oil, or any other value disclosed herein for this ratio.

When the microbial oil is a refined oil, preferably the triglyceride content is greater than or equal to 90% by weight. The weight ratio of arachidonic acid relative to dihomo-γ-linolenic acid is desirably less than or equal to 1/20 in the refined oil, or any other value disclosed herein for this ratio.

A further aspect is a lower alcohol ester composition comprising dihomo-γ-linolenic acid ester, or a free fatty acid composition comprising dihomo-γ-linolenic acid, produced or obtainable by a method comprising subjecting any microbial oil disclosed herein to an ester exchange reaction or hydrolysis reaction respectively.

A further aspect is a lower alcohol ester composition derived from a microbial oil and comprising dihomo-γ-linolenic acid ester, or a free fatty acid composition derived from a microbial oil and comprising dihomo-γ-linolenic acid, in which a weight ratio of arachidonic acid relative to dihomo-γ-linolenic acid (arachidonic acid/dihomo-γ-linolenic acid) is less than 1/13, or less than any other value disclosed herein for this ratio.

In the microbial oil, lower alcohol ester composition or free fatty acid composition of any of the present aspects the arachidonic acid content is usually less than or equal to 7% by weight and preferably much less, as discussed below.

The microbial oil, lower alcohol ester composition or free fatty acid composition of any of the present aspects may be provided for use as a medicament, preferably as an anti-allergic agent or an anti-inflammatory agent. The use as such a medicament is a further aspect of the present proposals. This aspect includes a method for the prevention, treatment or amelioration of inflammatory or allergic disease, or the substance for use in such method; the method comprising: administering a medicament including a microbial oil, lower alcohol ester composition or free fatty acid composition of any of the present aspects or preferred aspects, and preferably the purified dihomo-γ-linolenic acid or lower alcohol ester of dihomo-γ-linolenic acid, or composition containing it, to a subject suffering from, or at risk of suffering from, an inflammatory disease or allergic disease. The medicament may be administered topically or orally, preferably topically. The inflammatory disease or allergic disease may be, but without limitation, any of atopic dermatitis, allergic contact dermatitis (ACD), irritant contact dermatitis (ICD), photocontact dermatitis, systemic contact dermatitis, rheumatism, psoriasis, lupus and the like.

The microbial oil, lower alcohol ester composition or free fatty acid composition of any of the present aspects may in general be used in a method of producing foodstuffs, dietary supplements, medicaments, cosmetics or animal feed.

Further aspects of the invention are a microbial biomass containing any microbial oil as defined herein in combination with the microbial cells, and a liquid culture medium containing such a microbial biomass.

In such a liquid culture medium the content of the microbial biomass may greater than or equal to 2.5 g/L, in terms of dry weight of the microbial biomass.

Desirably the liquid culture medium contains the microbial oil at a content of 0.4 g/L or greater.

A further aspect of the invention provides methods for producing such microbial oils, and for the further processing thereof to useful products.

One method aspect is a method of producing a dihomo-γ-linolenic acid-containing microbial oil, such as any microbial oil disclosed herein, comprising:

adding Δ5 desaturase inhibitor, especially two or more two types of Δ5 desaturase inhibitor, to a liquid culture medium, and culturing a microbe having a reduced or lost Δ5 desaturation activity in the liquid culture medium to produce the dihomo-γ-linolenic acid containing microbial oil.

One of the at least two types of Δ5 desaturase inhibitor may be an aryl benzamide Δ5 desaturase inhibitor, especially 2-amino-N-(3-chlorophenyl)benzamide.

One of the at least two types of Δ5 desaturase inhibitor, or a said Δ5 desaturase inhibitor other than 2-amino-N-(3-chlorophenyl)benzamide, may be a dioxabicyclo[3.3.0] octane derivative represented by Formula (I):

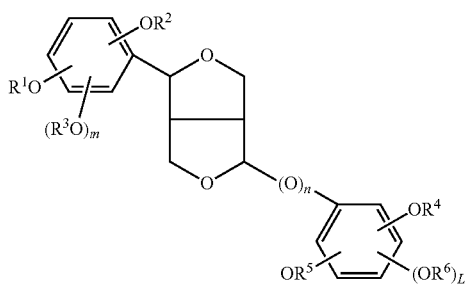

wherein, $R^1$, $R^2$, $R^3$, $R^4$, $R^5$, and $R^6$ are each independently a hydrogen atom or an alkyl group having from 1 to 3 carbon atoms; or, $R^1$ and $R^2$, and/or $R^4$ and $R^5$ together form a methylene group or an ethylene group, and n, m, and L represent 0 or 1;

piperonyl butoxide, curcumin, or a compound represented by Formula (II):

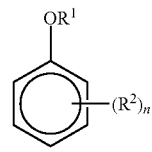

wherein, $R^1$ represents a lower alkyl group; $R^2$ represents a hydroxyl group, an alkyl group, an alkoxy group, an alkenyl group or an oxyalkyl group wherein in the case that a plurality of $R^2$ are present, the plurality of $R^2$ may be the same or different, and n is an integer of 0 to 5.

Where a dioxabicyclo[3.3.0] octane derivative used it is may be selected from sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0] octane, 2,6-bis-(3-methoxy-4-hydroxyphenyl)-3,7-dioxabicyclo [3.3.0] octane and 2-(3,4-methylenedioxyphenyl)-6-(3-methoxy-4-hydroxyphenoxy)-3,7-dioxabicyclo[3.3.0] octane.

Particularly, one of the at least two types of Δ5 desaturase inhibitor, or a said Δ5 desaturase inhibitor other than 2-amino-N-(3-chlorophenyl)benzamide, may be sesamin or curcumin.

In general the microbe used herein as source of the oil is most desirably a microbe belonging to the genus *Mortierella*. It may or not be genetically modified. It may be a microbe with an arachidonic acid-producing function which has been inhibited by reduced or lost Δ5 desaturation activity, e.g. by mutation and/or selection.

A further method aspect is a method of producing a lower alcohol ester composition or free fatty acid composition as proposed above, from any microbial oil as proposed herein, the method comprising:

(a) obtaining a mixture of fatty acids or lower alcohol esters of fatty acids by hydrolysis or alcoholysis respectively of the microbial oil, and (b) purifying the mixture of fatty acids or lower alcohol esters, preferably by rectifying, to obtain a fatty acid or lower alcohol ester composition in which the fatty acids have at least 20 carbon atoms.

This mixture or composition may be further purified e.g. by column chromatography such as reverse phase distribution type column chromatography. For example the lower alcohol dihomo-γ-linolenic acid ester or free dihomo-γ-linolenic acid may be purified or produced by producing a lower alcohol ester composition or free fatty acid composition as described and then performing fractionation and purification of the lower alcohol ester of dihomo-γ-linolenic acid, or of dihomo-γ-linolenic acid, by reverse phase distribution type column chromatography.

A further method aspect is a method of producing a lower alcohol ester composition or free fatty acid composition comprising dihomo-γ-linolenic acid, comprising:

(a) producing a dihomo-γ-linolenic acid-containing microbial oil by culturing a microbe in a liquid culture medium to produce the dihomo-γ-linolenic acid, the microbe being a microbe with an arachidonic acid-producing function which has been inhibited by reduced or lost Δ5 desaturation activity, optionally in the presence of one, two or more types of Δ5 desaturase inhibitor in the liquid culture medium, to produce said microbial oil in which a weight ratio of arachidonic acid relative to dihomo-γ-linolenic acid is less than 1/13;

(b) by hydrolysis or alcoholysis of the microbial oil, obtaining a mixture of fatty acids or lower alcohol esters containing dihomo-γ-linolenic acid, optionally after purification of the oil;

(c) purifying the mixture of fatty acids or lower alcohol esters.

In step (c) the mixture may be purified to obtain a fatty acid or lower alcohol ester mixture in which the fatty acids have at least 20 carbon atoms, and the method may further comprise (d) performing fractionation and purification of dihomo-γ-linolenic acid or lower alcohol ester of dihomo-γ-linolenic acid from said purified mixture by reverse phase chromatography.

The purified dihomo-γ-linolenic acid or lower alcohol ester of dihomo-γ-linolenic acid, or composition containing it, may be used in any manner described herein, e.g. used as or incorporated into a medicament, preferably an antiallergic agent or an anti-inflammatory agent.

EFFECT OF THE INVENTION

According to the present invention, a microbial oil and microbial biomass capable of use in order to efficiently obtain a dihomo-γ-linolenic acid-containing oil that has a lower arachidonic acid content than that of the oil obtained by a conventional method and use thereof can be provided.

According to the present invention, a method of producing a dihomo-γ-linolenic acid-containing lipid that has a lower arachidonic acid content than that of the oil obtained by a conventional method, and the free fatty acid of dihomo-γ-linolenic acid and a lower alcohol ester of dihomo-γ-linolenic acid that have the lower arachidonic acid content than those of the free fatty acid and the lower alcohol ester obtained by a conventional method can be provided.

According to other aspects of the present invention, uses of such dihomo-γ-linolenic acid-containing lipid, the free fatty acid of dihomo-γ-linolenic acid or the lower alcohol ester of dihomo-γ-linolenic acid are provided.

DESCRIPTION OF EMBODIMENTS

The microbial oil of the present invention is a microbial oil comprising DGLA as a constituent fatty acid of an oil and fat and having a content, in terms of a weight ratio of arachidonic acid relative to DGLA (ARA/DGLA), of less than 1/13.

The microbe of the present invention is a microbial biomass containing a microbial oil comprising DGLA as a constituent fatty acid of an oil and having a content, in terms of a weight ratio ARA relative to DGLA (ARA/DGLA), of less than 1/13.

Although the content ratio of DGLA and ARA may be defined as a weight ratio (ARA/DGLA), this may also be expressed as a weight ratio (DGLA/ARA). Since the oil often originates from a microbe having a native ARA-producing function, although this function may have been reduced by mutation or strain selection and/or inhibited in culture, at least a trace of ARA is often present.

According to the present invention, a microbial oil which contains DGLA and has a weight ratio of DGLA relative to ARA (DGLA/ARA) of greater than or equal to 13, and a microbial biomass which contains DGLA and has a weight ratio of DGLA relative to ARA (DGLA/ARA) of greater than or equal to 13 are provided. The microbial oil and microbial biomass having a DGLA/ARA (weight ratio) of greater than or equal to 13 have been unknown heretofore.

Thus, by use of the microbial oil of the present invention or by use of the microbial biomass of the present invention, it is possible to efficiently provide an oil that contains DGLA at higher DGLA purity and lower ARA content than conventional oils.

The microbial oil of the present invention is a lipid obtained by culturing a microbe that produces DGLA-containing lipids in a suitable culture medium and recovering from the microbial biomass using methods such as solvent extracting. In general, the lipids include triglycerides, diglycerides, monoglycerides, phospholipids, cholesterol, and the like, and the lipids are mainly composed of triglycerides. Various types of fatty acids are included as the constituent fatty acids of these lipids. In the microbial biomass and the microbial oil of the invention, among these constituent fatty acids, the content of DGLA is high and the content of ARA is low.

In the present invention, the term "crude oil" of microbial oil refers to a mixture of lipids as obtained simply by extraction of such lipids from the microbial biomass. The refined oil of microbial oil is a microbial oil obtained by refining this microbial oil to remove phospholipids and cholesterol and thereby increase the proportion of triglycerides. The term "microbial oil" in the present specification means both the crude oil and refined oil unless otherwise noted. In general, It is possible to further increase concentration of a desired fatty acid by converting the desired fatty acid to free fatty acids form or lower alcohol esters form using hydrolysis or esterification with lower alcohol esters and then refining the free fatty acids or lower alcohol esters thereof. It is known that, since ARA and DGLA have the same number of carbon atoms, i.e. 20 carbon atoms, and the number of double bonds is 4 and 3, the properties of these compounds are similar and it is extremely difficult to separate DGLA from ARA by a purification process realized at actual production scale. A microbial oil in which the ARA content is low at the stage of the crude microbial oil, in other word, the difference between a DGLA content and an ARA content is large, may be provided by the present invention and therefore can markedly increase the ability to obtain a very high DGLA/ARA in a refined and/or chemically-processed downstream form of the product.

The term "ARA/DGLA" or the term "DGLA/ARA" in the present specification is a weight ratio between ARA and DGLA according to analysis of the composition of fatty acids included in an oil. The composition of fatty acids may be determined by the conventional method. Specifically, the analyte oil is esterified using a lower alcohol and a catalyst to obtain fatty acid lower alcohol esters. Thereafter, the obtained fatty acid lower alcohol esters are analyzed using gas chromatography. The peaks corresponding to each of the fatty acids are identified in the obtained gas chromatogram, and the peak area of each of the fatty acids is determined, e.g. using the Agilent ChemStation integration algorithm (revision C.01.03 [37], Agilent Technologies). "Peak area" indicates the ratio of the peak area for a respective component to the area of all peaks, that is, the proportion of content of the component of the peak, as determined by the analytical chart obtained from gas chromatography or thin-layer chromatography/flame ionization detector (TLC/FID) of oil having various fatty acids as constituent components. The fatty acid composition was determined by gas chromatography, e.g. according to the method indicated in the Examples below. The lipid composition was determined using TLC/FID. Detailed suitable conditions are indicated in the working examples.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component type that may be included in the composition is indicated herein, when there are plural substances corresponding to the component type in the composition, the indicated amount means the total amount of the plural substances present in the composition, unless specifically stated otherwise.

In the present specification, the term "microbe" includes both eukaryotes and prokaryotes, as exemplified specifically by bacteria, actinomycetes, cyanobacteria, archaea, fungi, algae, lichens, protozoa, and the like.

For convenience the term "oil" is used herein in to refer to "oil/fat". Also, while the terms "oil" and "oil/fat" are sometimes narrowly defined as specifying triglycerides, in the present specification these terms are taken to include oils, e.g. crude oils, comprising triglycerides as a main component with other lipid components such as diglycerides, monoglycerides, phospholipids, cholesterol, and free fatty acids. Practically, the triglyceride content is preferably greater than or equal to 30% by weight, more preferably is greater than or equal to 50% by weight, further preferably is greater than or equal to 70% by weight, and most preferably is greater than or equal to 90% by weight.

In the present specification, the term "crude oil" means an oil in the state as obtained by extraction from the microbe, and being generally a mixture of the lipid components described above. In the present specification, the term "refined oil" is taken to mean an oil obtained after refining process, comprising degumming process, deacidification process, decoloring process (bleaching process), deodorization process and the like, in any combination of some or all of them, for removing substances other than the target substance, such as phospholipids and cholesterol. The skilled person is familiar with these terms and can distinguish crude microbial oils from refined microbial oils by reference to their specific composition. Particular refining steps remove characteristic subsets of impurities from the original crude microbial oil, which in itself can be generally characteristic of its microbial source as is known.

In the present specification, the term "microbial oil" is taken to widely mean any oil obtained from a microbe and is used in the present specification without distinguishing between crude oils and refined oils, unless otherwise noted.

In the present specification, the expression "microbial biomass containing microbial oil" means biomass having the microbial oil accumulated within the microbial cells or released from the microbial cells by culturing the microbes that produces the microbial oil of the present invention. Both living microbes and dead microbes may be included in the microbial biomass. Dried microbial biomass is also included. The expression "dried microbial biomass" is taken to mean a dried product of microbial biomass including substantially no water as well as the dried product including residual culture medium components, filtration aids, and the like. The expression "including substantially no water" means that the moisture content is at or below the amount that would result in difficulty for the microbe to live. This amount is generally less than or equal to 15% by weight moisture content, and preferably is less than or equal to 10% by weight moisture content.

In the present specification, the expression "liquid culture medium including the microbial biomass" is the liquid culture medium in which the "microbial biomass" described above is cultured, and this refers to the state prior to separation of the microbial biomass from the culture liquid.

Aspects of the present invention will be described below.

(1) Microbial Oil

The microbial oil of the present invention includes DGLA and has a DGLA/ARA (weight ratio) of greater than or equal to 13. The value of DGLA/ARA is preferably as high as possible, further preferably is greater than or equal to 15, greater than or equal to 20, or greater than or equal to 30, and still further preferably is greater than or equal to 50, still further preferably is greater than or equal to 100, and particularly preferably is greater than or equal to 200. When the value of DGLA/ARA is less than 13, the relative proportion of ARA in the microbial oil relative to DGLA becomes high, and even if the microbial oil is refined or the like, the resultant ARA content may be near 10% by weight so that DGLA purity can be insufficiently increased by purification. No particular limitation is placed on the upper limit of DGLA/ARA in the microbial oil, and for example, the value of DGLA/ARA may be set less than or equal to 3,000.

The content of DGLA in the microbial oil may be 10% by weight or more, preferably 15% by weight or more, more preferably 20% by weight or more, further preferably 25% by weight or more, based on the total weight of the microbial oil. The microbial oil may have a little of ARA. The content of ARA in the microbial oil may be 0.03% by weight or more, 0.01% by weight or more, 0.001% by weight or more, or 0.0005% by weight or more. The content of ARA in the microbial oil is preferably not more than 10% or not more than 7% by weight.

Moreover, the content of triglyceride in the crude oil with respect to the total amount of the microbial oil is preferably greater than or equal to 70% by weight in the microbial oil described above, and more preferably is greater than or equal to 90% by weight. When the content of triglycerides in the microbial oil is greater than or equal to 70% by weight, there is a tendency for moisture absorption not being excessively low, such that e.g. good flowability may be obtained. Although no particular limitation is placed on the upper limit of the content of the triglyceride in the microbial oil, generally the weight content of triglycerides in the microbial oil is less than or equal to 99% by weight. The weight content of triglycerides in the microbial oil may be 100% by weight, that is, the microbial oil may contain substantially no non-triglyceride components. The fatty acids constituting the triglycerides of the microbial oil are exemplified by saturated or unsaturated fatty acids having 14 to 26 carbon atoms. The refined oil may have an increased concentration of triglycerides due to removal of impurities e.g. by known methods.

In the fatty acid composition of the crude microbial oil, with respect to the total weight of the microbial oil, the microbial oil preferably contains less than or equal to 60% by weight of fatty acids having 18 carbon atoms or less. This content is more preferably less than or equal to 55% by weight, and this content is further preferably less than or equal to 50% by weight. Oil having a low content of fatty acids having 18 or less carbon atoms in the crude oil is preferable since the oil may be used as triglyceride without the need to adjust the fatty acid composition by removing fatty acids having 18 or less carbon atoms. Such adjustment generally needs a method with low yield such as winterizing (low temperature processing) or the like.

The microbial oil preferably has a phospholipid content less than or equal to 10% by weight with respect to the total weight of the oil, especially for the crude microbial oil, and more preferably 5% by weight, further preferably less, than or equal to 1% by weight with respect to the total weight of the oil. However phospholipid may be present to some extent, such as from 0.1 to 10% by weight, more preferably 0.5 to 7% by weight, still more preferably 1 to 5% by weight with respect to the total weight of the oil.

The saturated fatty acid content of the microbial oil is preferably less than or equal to 40% by weight with respect to the total weight of the crude microbial oil, and more preferably is less than or equal to 35% by weight of the crude microbial oil. A microbial oil having a low content of saturated fatty acids is favorable for some uses, such as a functional dietary supplement.

It should be understood that the above-described optional values for the various parameters of the microbial oil are generally independently achievable and may be freely combined to define preferred microbial oils.

(2) Production of Microbial Oil

The microbial oil may be obtained by a production method including producing microbial oil by culturing a microbe known to produce lipids (referred to hereinafter as the production process), and separating the obtained microbial oil from the microbial biomass (separation process).

DGLA containing lipid may be obtained by a production method including producing microbial oil by culturing a microbe known to produce lipids (referred to hereinafter as the production process), and separating the obtained microbial oil from the microbial biomass (separation process).

The producing method of DGLA-containing lipid or the producing method of microbial oil according to the present invention may be a method including adding two or more types of Δ5 desaturase inhibitors to a liquid culture medium and culturing a microbe having a reduced or lost Δ5 desaturation activity in the liquid culture medium to produce the dihomo-γ- linolenic acid containing lipids.

Alternatively, the producing method of DGLA containing lipid or the producing method of microbial oil according to the present invention may be a method including adding two or more types of Δ5 desaturase inhibitors to a liquid culture medium; and culturing a microbe, having a reduced or lost Δ5 desaturation activity obtained by mutating a microbe capable of producing arachidonic acid, in the liquid culture medium to produce the dihomo-γ-linolenic acid-containing lipids.

In other words, the producing method of DGLA-containing lipid or the producing method of microbial oil according to the present invention may be a method of producing lipids having a lowered arachidonic acid content relative to dihomo-γ-linolenic acid in the lipids by culturing a microbe, obtained by mutating a microbe capable of producing arachidonic acid, having a reduced or lost Δ5 desaturation activity, to produce lipid containing dihomo-γ-linolenic acid and the method comprising adding e.g. two types of Δ5 desaturase inhibitors to a culture liquid of the microbe.

The microbe known to produce lipids used in the production process is preferably at least one kind selected from the group consisting of microbes of the genera *Mortierella, Conidiobolus, Pythium, Phytophthora, Penicillium, Cladosporium, Mucor, Fusarium, Aspergillus, Rhodotorula, Entomophthora, Echinosporangium*, and *Saprolegnia*. The microbe should be a microbe that has the ability to produce DGLA, and a microbe belonging to the genus *Mortierella* is further preferred.

The microbe is further preferably a microbe having reduced or lost Δ5 desaturation activity (referred to hereinafter as a "low Δ5 desaturation activity microbe"), such as reduced or lost Δ5 desaturation activity relative to a native state. More preferably it is a microbe having having reduced or lost Δ5 desaturation activity obtained by mutation of a microbe having an ARA production function, and further more preferably a microbe belonging to the genus *Mortierella* and having reduced or lost Δ5 desaturation activity obtained by mutation in/of a microbe having an ARA production function. The microbe having an ARA production function for the mutation is preferably a microbe of the genus *Mortierella* having an ARA production function.

Microbes of the genus *Mortierella* having an ARA production function are exemplified by microbes belonging to the subgenus *Mortierella*, such as *Mortierella elongata, Mortierella exigua, Mortierella hygrophila*, and *Mortierella alpina*. The low Δ5 desaturation activity microbe may be obtained by introducing mutation into a microbe having an ARA production function, inducing a mutant strain that has reduced or lost Δ5 desaturase activity.

Examples of mutation procedure include physical treatments such as by irradiation (X-rays, gamma rays, neutron beam, or the like), ultraviolet irradiation, and heat treatment.

Moreover, the target mutant strain may be obtained by a mutant strain isolation method, comprising incubating the microbe targeted for mutation for a fixed time interval in the presence of a source of mutation and inoculating in agar medium according to the standard method to obtain a colony of the target mutant strain. Examples of the source of mutation used in the mutant strain isolation method include alkylating agents such as nitrogen mustard, methyl methane sulfonate (MMS), N-methyl-N'-nitroso-N-nitrosoguanidine (NTG); base analogs such as 5-bromouracil; antibiotics such as mitomycin C; inhibitors for base synthesis such as 6-mercaptopurine; dyes such as proflavine; cancer-causing agents such as 4-nitroquinoline-N-oxide; and manganese chloride, potassium dichromate, nitrous acid, hydrazine, hydroxylamine, formaldehyde, nitrofuran compounds and the like. Moreover, the form of the microbe targeted for mutation may be the growing microbial body (mycelia or the like) or spores.

For example, among low Δ5 desaturation activity microbes, the mutant strain *Mortierella alpina* SAM 1860 (Accession Number 3589 at the Fermentation Research Institute), induced by mutation in the aforementioned manner, may be used as the mutant strain of the genus *Mortierella*. The production of DGLA using SAM 1860 is described in detail in JP-A No. H05-091887. This production method is summarized below.

In order to culture the low Δ5 desaturation activity microbe, the spores or mycelia of the microbial strain or precultured liquid culture medium obtained by culturing in advance are used to inoculate into a liquid or solid medium, and the microbe is cultured.

In a case of a liquid medium, any of generally used carbon sources including glucose, fructose, xylose, saccharose, maltose, soluble starch, molasses, glycerol, mannitol, and the like, can be used; however, the carbon source is not limited to these.

The nitrogen source can be a natural nitrogen source such as peptone, yeast extract, malt extract, meat extract, casamino acid, corn steep liquor, as well as organic nitrogen sources such as urea, and inorganic nitrogen sources such as sodium nitrate, ammonium nitrate, ammonium sulfate. In addition, inorganic salts such as phosphates, magnesium sulfate, iron sulfate, copper sulfate, as well as vitamins or the like can also be used as trace nutrient source, if necessary.

An aqueous medium used as the base material for the liquid medium is basically water, and distilled water or purified water may be used.

No particular limitation is placed on these culture media components as long as the concentration of these components does not interfere with the growth of the low $\Delta 5$ desaturation activity microbe. Generally, for practical purposes, the concentration of carbon source is from 0.1% by weight to 30% by weight, and preferably from 1% by weight to 10% by weight, and the concentration of nitrogen source is from 0.01% by weight to 5% by weight, and preferably from 0.1% by weight to 2% by weight. Moreover, the culture temperature is from 5° C. to 40° C., and preferably is from 20° C. to 30° C. The pH of the culture medium is from 4 to 10, and preferably is from 6 to 9. Culturing may be an aeration-stirring culturing, shaking culturing, or stationary culturing. Culturing is usually performed for 2 days to 15 days. The aeration rate during aeration-stirring culturing may be a usually used aeration rate for such aeration.

In order to promote the accumulation of DGLA, a component to be a substrate for the production of ARA and/or DGLA may be added to the culture medium. Such substrates are exemplified by hydrocarbons such as tetradecane, hexadecane, octadecane; fatty acids such as tetradecanoic acid, hexadecanoic acid, octadecanoic acid; salts of such fatty acids, such as sodium salts and potassium salts; fatty acid esters; oils-fats containing fatty acids as constituent components, such as olive oil, soybean oil, cottonseed oil, and palm oil; and the like. However, the substrate is not limited to these.

A conventional solid medium may be used as the solid medium for culturing the low $\Delta 5$ desaturation activity microbe. Such solid media are exemplified by agar culture medium, malt extract agar culture medium, malt agar culture medium, Czapek-Dox agar culture medium, Czapek agar culture medium, potato-carrot agar culture medium (PCA), potato-glucose agar culture medium ("Potato Dextrose Agar Culture Medium" as tradename, potato dextrose agar: PDA), Sabouraud agar culture medium, cornmeal agar culture medium, and the like. The culture medium may be selected appropriately according to the species of the microbe used for culturing. Any of such solid culture media may be available as commercially marketed products, and the commercial solid culture medium may be used without any modification and according to the instructions provided therewith. Among such solid culture media, PDA culture medium is preferred from the standpoint of efficient production of DGLA in the low $\Delta 5$ desaturation activity microbe.

In order to produce a microbial oil having a higher DGLA/ARA ratio, a culture medium used for culturing of the microbe is preferably a liquid medium comprising glucose as the carbon source and yeast extract as the nitrogen source in the case of liquid medium, or PDA culture medium in the case of a solid medium.

(3) Culturing of the Microbe

In order to produce a microbial oil having a higher DGLA/ARA ratio, the microbe, preferably a low $\Delta 5$ desaturation activity microbe, is preferably cultured in the presence of a $\Delta 5$ desaturase inhibitor. The $\Delta 5$ desaturase inhibitor inhibits an enzyme in the synthesis pathway leading to ARA during production of fatty acids in the microbial cell. Thus, by use of the $\Delta 5$ desaturase inhibitor(s) and/or selection of a suitable microbe which favors DGLA over ARA production, e.g. a mutated ARA producer according to the known principles, the synthesis of ARA in the microbial cells may be inhibited and increase markedly the accumulated amount of DGLA in the microbial cells.

Any known $\Delta 5$ desaturase inhibitor may be used without any limitation, as one type or as a combination of two or more types. In order to more efficiently obtain the high DGLA/ARA microbial oil, the inventors find that a combination of two or more $\Delta 5$ desaturase inhibitors is preferably used. Surprisingly the inventors have found that they can achieve a marked increase in the DGLA/ARA ratio by such combinations, which would not have been foreseen, to produce novel microbial oils with unprecedentedly high DGLA/ARA ratio.

In a case in which a combination of two types of $\Delta 5$ desaturase inhibitors is used, 2-amino-N-(3-chlorophenyl) benzamide is preferably selected as the first type of $\Delta 5$ desaturase inhibitor. By combination of 2-amino-N-(3-chlorophenyl) benzamide with another type of $\Delta 5$ desaturase inhibitor, the reducing of the overall production amount of lipid is suppressed, and the DGLA/ARA ratio may be increased. 2-amino-N-(3-chlorophenyl)benzamide is an anthranilic anilide, known as an aryl benzamide having $\Delta 5$ desaturase inhibitor effect which may be used here, but it was not previously known to be effective for the present type of process.

The second type of $\Delta 5$ desaturase inhibitor may be exemplified by a dioxabicyclo [3.3.0] octane derivative represented by following Formula (I):

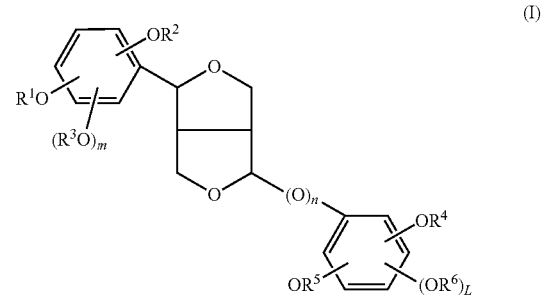

wherein, in the formula (I), $R^1$, $R^2$, $R^3$, $R^4$, $R^5$, and $R^6$ represent each independently a hydrogen atom or an alkyl group having from 1 to 3 carbon atoms; alternatively, $R^1$ and $R^2$ and/or $R^4$ and $R^5$ together form a methylene group or an ethylene group; and n, m, and L represent 0 or 1;

piperonyl butoxide, curcumin, and a compound represented by following Formula (II) below:

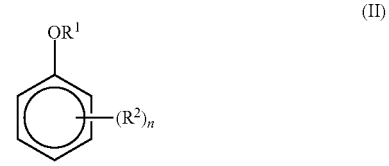

wherein, in the formula (II), $R^1$ represents a lower alkyl group, such as an alkyl group having from 1 to 3 carbon atoms; $R^2$ represents a hydroxyl group, an alkyl group, an alkoxy group, an alkenyl group, or an oxyalkyl group; in the case that a plurality of $R^2$ are present, the plurality of $R^2$ may be the same or different; and n is an integer in a range of 0 to 5, or the like. Such Δ5 desaturase inhibitors may be used alone or in combination.

The dioxabicyclo [3.3.0] octane derivative may be exemplified by sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane, and the like. Such dioxabicyclo [3.3.0] octane derivatives may be used alone or as a combination of two or more types. Moreover, such dioxabicyclo [3.3.0] octane derivatives may be used in combination with a stereoisomer or a racemate. Particularly preferably, the dioxabicyclo [3.3.0] octane derivative is at least one type selected from the group consisting of sesamin and curcumin. Such dioxabicyclo [3.3.0] octane derivatives may be products of chemical synthesis or extracts from natural products.

No particular limitation is placed on the adding manner of the Δ5 desaturase inhibitor other than 2-amino-N-(3-chlorophenyl)benzamide added to the culture medium, and this manner may be selected appropriately according to the type and form of the utilized Δ5 desaturase inhibitor. For example, the Δ5 desaturase inhibitor may be at least one, type selected from sesame oil, peanut oil, and natural extracts such as extracts from sesame oil using organic solvents substantially incompatible with sesame oil, solvent extracts of sesame seed, extract of Acanthopoanacis Core (gokahi extract), extract of Paulownia tree, ginkgo bark extract, Piper longum extract, Asiasari radix extract, tarragon extract, dill seed extract, parsley extract, turmeric extract, and nutmeg extract. In the case in which the Δ5 desaturase inhibitor is a natural extract, such natural extracts may be added to the culture medium used for culturing the microbe, or alternatively, these natural extracts may be added to the liquid culture medium culturing the microbe. The microbe may be further cultured using a culture medium containing these Δ5 desaturase inhibitors.

In a case in which a combination of two or more types of Δ5 desaturase inhibitor is used, this combination may be a combination of 2-amino-N-(3-chlorophenyl)benzamide (or one of the other first type inhibitors listed earlier) and at least one type of Δ5 desaturase inhibitor selected from the group consisting of the dioxabicyclo[3.3.0] octane derivatives, piperonyl butoxide, curcumin and the compounds represented by the Formula (II). From the standpoint of obtaining a microbial oil having a high DGLA/ARA ratio, the combination of 2-amino-N-(3-chlorophenyl)benzamide and the dioxabicyclo[3.3.0] octane derivative is preferred. A combination of 2-amino-N-(3-chlorophenyl)benzamide and at least one selected from the group consisting of sesamin, sesaminol, episesamin, episesaminol, sesamolin, 2-(3,4-methylenedioxyphenyl)-6-(3-methoxy-4-hydroxyphenyl)-3, 7-dioxabicyclo[3.3.0] octane, 2,6-bis-(3-methoxy-4-hydroxyphenyl)-3,7-dioxabicyclo[3.3.0] octane, and 2-(3,4-methylenedioxyphenyl)-6-(3-methoxy-4-hydroxyphenoxy)-3,7-dioxabicyclo[3.3.0] octane is more preferred.

Although the added concentration of the Δ5 desaturase inhibitor depends on the type of the utilized Δ5 desaturase-inhibitor, in the case of a liquid medium, the added concentration in the liquid culture medium of Δ5 desaturase inhibitor per day is preferably from 0.01 g/L to 1 g/L, and more preferably is from 0.03 g/L to 0.50 g/L. Moreover, in the case of a solid medium, the respective concentration of the Δ5 desaturase inhibitor is preferably 0.0001% by weight to 0.1% by weight, and more preferably is 0.001% by weight to 0.05% by weight. In a case in which the Δ5 desaturase inhibitor is used in the form of sesame oil or an extract such as sesame oil extract, in consideration of factors such as the amount of effective component included in the extract, the final concentration of the total amount of Δ5 desaturase inhibitors in the liquid culture medium, for example, is 0.001% by weight to 10% by weight, and preferably is 0.5% by weight to 10% by weight. In a case in which a combination of two or more types of Δ5 desaturase inhibitors is used, no particular limitation is placed on the ratios of the amounts of the utilized multiple Δ5 desaturase inhibitors, and such ratios may be selected appropriately according to the types of the utilized Δ5 desaturase inhibitors. For example, in the case in which 2-amino-N-(3-chlorophenyl) benzamide is used in combination with another Δ5 desaturase inhibitor, the ratio of 2-amino-N-(3-chlorophenyl)benzamide or other benzamide to the other Δ5 desaturase inhibitor (effective component in the natural extract, in the case of a natural extract) may be, in terms of weight ratio, from 100:1 to 1:100, and preferably from 10:1 to 1:10, and more preferably is from 5:1 to 1:5.

The production of lipids by the microbe may be affected in the case in which the Δ5 desaturase inhibitor is added to the culture medium, and in this case, in order to lessen the effect on production, it is preferable to add the Δ5 desaturase inhibitor to the culture liquid in aliquots rather than as the entire amount.

No particular limitation is placed on the time of addition of the Δ5 desaturase inhibitor, and such addition may be performed every day, or may be performed once a day to once a few days during the culturing of the microbe. In a case in which the Δ5 desaturase inhibitor is added at intervals of once a day to once a few days, additions may be performed at equally spaced intervals, at irregularly spaced intervals, or at a combination of such intervals. The time of addition of the Δ5 desaturase inhibitor may be selected appropriately according to the growth state of the microbe.

In a case in which the Δ5 desaturase inhibitor is added to the culture medium during the production process, in order to produce microbial oil having a higher DGLA/ARA ratio, for the culture medium used during the production process, in the case of a liquid medium, the liquid medium in which uses glucose as a carbon source and yeast extract as a nitrogen source is preferred, and, in the case of a solid medium, PDA culture medium is preferred.

No particular limitation is placed on the culture vessel used in the production process, and any culture vessel may be used that is usually used for the culturing of microbes. The culture vessel may be selected appropriately according to the scale of culturing.

For example, in the case of liquid culturing at the 1 L to 50 L scale, a stirred type culture vessel is preferred as the culture vessel in order to produce a microbial oil having a higher DGLA/ARA ratio. The stirred type culture vessel preferably has disc turbine type agitator blade in at least one stage, and a stirred type culture vessel further preferably has disc turbine type agitator blades in two stages. In the case of a stirred type culture vessel equipped with disc turbine type agitator blades in two stages, the distance between the agitator blades that are closer to the bottom surface may be small in order to efficiently stir the culture liquid efficiently at the culture vessel bottom surface. For example, the positions of placement of the upper and lower agitator blades may be selected appropriately. For example, the ratios of "distance from the culture vessel bottom to the lower agitator blade": "distance between the lower agitator blade and the upper agitator blade": "distance from the upper agitator blade to the surface of the culture liquid" are preferably adjusted to become "1": "1 to 3": "1 to 5", preferably "1": "1.5 to 2": "2 to 4". A preferred example of these ratios is 4:7:15. The stirring type culture vessel is particularly preferred in the case of culturing the microbe using a liquid culture medium containing the culture medium including Δ5 desaturase inhibitor.

(4) Separation of Microbial biomass from the Culture Medium, and Recovering of the Microbial Oil from the Microbial biomass In the separation process, the microbial oil containing DGLA produced during the production process is separated from the microbial biomass. The separation process preferably includes separation of the cultured microbial biomass from the culture medium used in culturing (microbial biomass separation process) and recovery of the microbial oil containing DGLA from the cultured microbial biomass (recovering process), that is, the obtaining of the crude oil.

In the microbial biomass separation process and the microbial oil recovering process, an extraction method and a separation method are used according to the manner of culturing, so that the DGLA-containing microbial oil is recovered from the cultured microbial mass.

In a case in which a liquid medium is used, the microbial oil containing DGLA is recovered, for example, in the following manner from the cultured microbial biomass.

After completion of culturing, the cultured microbial biomass is obtained from the liquid culture medium by use of a normal means for solid-liquid separation such as a centrifugal separation and filtration. The microbial biomass is washed sufficiently using water, and then is preferably dried. Drying may be performed by freeze drying, air-drying, heating-drying, or the like.

In a case in which a solid medium is used for culturing, the solid medium and microbial biomass may be crushed using a homogenizer or the like without separation of the microbial mass from the culture medium, and the obtained crushed material may be directly supplied to the recovering process.

The recovering process may include extraction processing of the dried microbial biomass obtained in the microbial biomass separation process by using an organic solvent, preferably under nitrogen gas stream. The utilized organic solvent includes ether, hexane, methanol, ethanol, chloroform, dichloromethane, petroleum ether, and the like. Alternatively, a good result may be obtained by alternating extraction using methanol and petroleum ether, or extraction using a single layer type solvent of chloroform-methanol-water. A microbial oil containing a high concentration of DGLA is obtained by distilling off the organic solvent from the extract under reduced pressure. Hexane is most generally used in the case of recovering triglycerides.

Moreover, as an alternative to the aforementioned method, extraction may be performed using the moist microbial biomass. A solvent that is miscible with water, such as methanol or ethanol, or a mixed solvent miscible with water, containing the solvent and water and/or other solvent, is used. The remainder of the procedure is similar to that described above.

The crude oil of the recovered microbial oil may be refined by a method which is used for refining plant oils, fish oils, or the like. Normally used refining process for oils/fats are exemplified by degumming, deacidification, bleaching (decolorization), and deodorization process. Such processing may be performed by any method. Degumming is exemplified by water wash treatment. Deacidification is exemplified by distillation treatment. Bleaching is exemplified by bleaching using activated clay, activated carbon, silica gel, or the like. Deodorization is exemplified by steam distillation or the like.

(5) Production of Lower Alcohol Esters and Free Fatty Acids of the fatty acid from the Microbial Oil The DGLA included as a constituent fatty acid of the microbial oil may be converted to a form of a lower alcohol ester by use of a catalyst, or a form of a free fatty acid by hydrolyzation. In comparison to triglyceride as is, the lower alcohol ester or the free fatty acid may be readily separated from other fatty acids, and it is possible to concentrate DGLA to increase their purity.

A method of producing a lower alcohol ester or free fatty acid of the dihomo-γ-linolenic acid according to the present invention may be a method comprising: (a) obtaining free fatty acids or lower alcohol esters of fatty acids by hydrolysis or alcoholysis of the microbial oil; (b) rectifying a mixture of the free fatty acids or the lower alcohol esters of the fatty acids to obtain a free fatty acid or lower alcohol ester of the fatty acids, which the fatty acids has at least 20 carbon atoms; and (c) performing fractionation and purification of free fatty acid or lower alcohol ester of dihomo-γ-linolenic acid by reverse phase distribution type column chromatography from the free fatty acid or lower alcohol ester, which the fatty acids has at least 20 carbon atoms.

A method of producing a lower alcohol ester of the dihomo-γ-linolenic acid according to the present invention may be a method comprising: (a) obtaining lower alcohol esters of fatty acids by alcoholysis of the microbial oil; (b) rectifying a mixture of the lower alcohol esters of the fatty acids to obtain a lower alcohol ester of the fatty acids, which the fatty acids has at least 20 carbon atoms; and (c) performing fractionation and purification of lower alcohol ester of dihomo-γ-linolenic acid by reverse phase distribution type column chromatography from lower alcohol ester, which the fatty acids has at least 20 carbon atoms.

A method of producing a free fatty acid of the dihomo-γ-linolenic acid according to the present invention may be a method comprising: (a) obtaining free fatty acids by hydrolysis of the microbial oil; (b) rectifying a mixture of the free fatty acids to obtain a free fatty acid having at least 20 carbon atoms; and (c) performing fractionation and purification of free dihomo-γ-linolenic acid by reverse phase distribution type column chromatography from the free fatty acid having at least 20 carbon atoms.

The lower alcohol herein is exemplified by alcohols having 3 or less carbon atoms, particularly ethanol, methanol, or the like. The lower alcohol esters of DGLA are exemplified by methyl dihomo-γ-linolenate, ethyl dihomo-γ-linolenate, and the like.

For example, the methyl esters of the fatty acids are obtained by treatment of the oil with from 5% to 10% of anhydrous methanol-hydrochloric acid, from 10% to 50% of $BF_3$-methanol, or the like, at room temperature for 1 to 24 hours. The ethyl esters of the fatty acids are obtained by treatment of the oil with from 1% to 20% of sulfuric acid ethanol or the like, for 15 to 60 minutes at 25° C. to 100° C. The methyl esters or the ethyl esters may be extracted from the reaction liquid using an organic solvent such as hexane, ether, or ethyl acetate. The extract liquid is dried using anhydrous sodium sulfate or the like, and then the organic solvent is removed by distillation to obtain a composition comprising fatty acid esters as main components.

In addition to the target DGLA lower alcohol ester, other fatty acid lower alcohol esters are included in the esterified composition obtained by esterification treatment. For isolation of the DGLA lower alcohol ester from the mixture of these fatty acid lower alcohol esters, distillation method, rectification method, column chromatography, low temperature crystallization method, urea clathrate method, liquid-liquid countercurrent distribution chromatography, or the like may be used by solely or a combination of two or more. A combination of distillation or rectification, and column chromatography or liquid-liquid countercurrent distribution chromatography is preferably used.

For these methods, normal procedures may be applied. Reverse phase distribution type (preferably ODS) column chromatography is preferred as the column chromatography.

In order to obtain the free fatty acid of DGLA, after the lower alcohol ester of the microbial oil is produced in the aforementioned manner, DGLA lower alcohol ester which is refined to increase the purity, may be hydrolyzed to obtain high purity free DGLA. In order to obtain free DGLA from the DGLA lower alcohol ester, after hydrolysis using an alkaline catalyst, extraction process may be carried out using an organic solvent such as ether, ethyl acetate, or the like.

Alternatively, the free fatty acid of DGLA may also be obtained directly from the microbial oil by hydrolysis. For example, the microbial oil undergoes alkaline decomposition, for example, for 2 to 3 hours at room temperature using 5% sodium hydroxide to obtain a decomposed liquid, and then the free fatty acid of DGLA may be extracted or refined from the decomposed liquid by the methods usually used for extraction or refining of fatty acids.

The free acid or lower alcohol ester of DGLA obtained by the aforementioned method is produced using the microbial oil of the present invention as the raw material, and thus the free acid or lower alcohol ester of DGLA is a composition having a low content of ARA, which is difficult to remove in the refining process. The ARA/DGLA ratio may be made less than 1/13, less than 1/20, or less than 1/30; or further may be made less than 1/50, less than 1/100, less than 1/200, less than 1/1,000, or less than 1/3,000. That is, the concentration of ARA may be made less than or equal to 7% by weight, less than or equal to 5% by weight, less than or equal to 3% by weight, less than or equal to 2% by weight, less than or equal to 1% by weight, less than or equal to 0.5% by weight, less than or equal to 0.1% by weight, or less than or equal to 0.03% by weight. For medical use, DGLA is preferably concentrated to greater than or equal to 90% by weight.

(6) Microbial Biomass Containing Microbial Oil

The expression "microbial biomass containing microbial oil" refers to a biomass of a microbe which produces microbial oil within its cells by cultivation in the above-described manner. The microbial biomass may be a microbial biomass having the microbial oil accumulated within the microbial cells, or after release of the oil from the microbial cells, as long as the microbial biomass comprises a microbial oil of the present invention. Because this microbial mass contains a microbial oil of the present invention, the microbial biomass contains DGLA as a constituent fatty acid of the oil and has a content of ARA relative to DGLA of greater than or equal to 13 as indicated by the weight ratio (DGLA/ARA). Furthermore, the microbial oil has preferably a triglyceride content of greater than or equal to 70% by weight, greater than or equal to 80% by weight or greater than or equal to 90% by weight.

Alternatively, the DGLA/ARA ratio of the microbial oil included in the microbial biomass of the present invention is preferably greater than or equal to 15, more preferably greater than or equal to 20, further preferably greater than or equal to 30, still further preferably greater than or equal to 50, still further preferably greater than or equal to 100, and particularly preferably greater than or equal to 200.

The DGLA/ARA ratio in the microbial biomass is taken to be the value determined in the aforementioned manner. Any method may be used for measurement of DGLA and ARA in the microbial biomass, as long as the method is one normally used for measurement of relative weights of DGLA and ARA in a microbial biomass, or equivalent. For example, the microbes may be recovered from the liquid culture medium during growth, and esterification treatment may be performed by 5% to 10% of anhydrous methanol-hydrochloric acid, 10% to 50% of $BF_3$-methanol, 1% to 20% sulfuric acid-methanol, 1% to 20% of sulfuric acid-ethanol, or the like for 15 minutes to 60 minutes treatment at 25° C. to 100° C. Then, analysis of the fatty acid content (%) in the fatty acids may be performed using gas chromatography with or without extraction of the ester forms. In the case of esterification for evaluation of substances other than the free fatty acids, treatment for 15 to 60 minutes at 25° C. to 100° C. using an alkoxide such as sodium methoxide, sodium ethoxide, or the like at a concentration of 0.1 M to 10 M may be used. For extraction of the ester form after esterification, an organic solvent which is immiscible with the water soluble component, such as hexane, may be used.

Moreover, the microbe is preferably a microbe capable of providing an oil that satisfies at least one condition, and preferably any combination of two or more conditions, from among conditions such as the triglyceride content, content of fatty acids having less than 18 carbon atoms, content of phospholipids, content of saturated fatty acids, and the like that are described above for the microbial oil.

(7) Liquid Culture Medium Containing Microbial Biomass Containing the Microbial Oil The "liquid culture medium containing microbial biomass containing the microbial oil" is taken to mean the culture medium prior to separation from the liquid culture medium of microbes grown by the microbial oil production method described above. Therefore, the liquid culture medium contains the DGLA described above and microbial oil having a DGLA/ARA ratio greater than or equal to 13. In order to recover the microbial oil from this liquid culture medium, the liquid culture medium preferably has the microbe content, in terms of a weight of the dried microbial biomass, of greater than or equal to 2.5 g/L. Furthermore, the content of the microbes in the microbe-containing liquid culture medium, in terms of a weight of the dried microbial biomass, is preferably greater than or equal to 5 g/L, more preferably greater than or equal to 30 g/L, and further more preferably greater than or equal to 60 g/L. It is possible to efficiently obtain microbial oil having a high DGLA/ARA ratio from such liquid culture medium.

Moreover, considering the microbial oil in the microbial mass in the liquid culture medium, the liquid culture medium contains the microbe-derived oil described above, which includes DGLA and has preferably the content of the oil containing DGLA of greater than or equal to 0.4 g/L, more preferably greater than or equal to 0.8 g/L. In a case in which the content of the oil containing microbial oil-derived DGLA is greater than or equal to 0.4 g/L, there is a tendency for advantages to be obtained such as decreasing of production costs, improvement of quality stability, and the like.

The microbe is grown by cultivation, and the DGLA is produced in the microbial cells. Therefore, by recovery of the liquid culture medium containing the microbes without any modification during the culturing process, the liquid culture medium containing the microbe may be obtained. Moreover, due to production of the microbial oil containing DGLA within the microbial cells of the microbe during the culture process, the microbial oil-containing liquid culture medium may be obtained by recovering the liquid culture medium containing microbes without any modification during the culture process, or alternatively, disrupting the microbes in the liquid culture medium by crushing or the like and recovering the liquid culture medium containing microbial oil released into the culture medium. Furthermore, with regard to the liquid culture medium in the liquid culture medium containing the microbial oil and the microbe-containing culture medium the above descriptions thereof may be applied as they are.

Applications

According to the present invention, the DGLA-containing microbe, the microbial oil, the lower alcohol esters, the free fatty acids, and the microbe-containing culture liquid can each have a ratio of ARA to DGLA that is lower than that previously known. Therefore, each is extremely useful for use in applications requiring high purity DGLA or for which the lower content of ARA is preferable. Such applications are exemplified by foodstuffs, dietary supplements, medicament, cosmetics, animal feeds, and the like. Since the DGLA-containing microbial oil has a low content of ARA, comparing to a DGLA-containing microbial oil having a high content of ARA, the amount of ARA in the microbial oil may be reduced for the same amount of microbial oil and DGLA to be used. Therefore, applications targeting the functionality of DGLA are particularly preferred, and such applications are exemplified by anti-inflammatory applications and anti-allergy applications, in particular topical applications, and the like, as set forth above.

As mentioned above the medicament comprising or consisting of the microbial oil, lower alcohol ester composition or free fatty acid composition may usually be administered topically or orally, preferably topically. An inflammatory disease or allergic disease to be treated, prevented or ameliorated may be for example, without limitation, any skin inflammation. Skin inflammation may be at least one selected from a group consisting of rashes, hives, blisters and wheals, or may be caused by at least one selected from a group consisting of eczema, exposure to radiation, automimmune diseases, and uremic pruritus.

In particular the skin inflammation may be skin inflammation associated with or caused by atopic eczema, contact dermatitis, psoriasis or uremic pruritis.

The medicament may be for the treatment, prevention or amelioration of skin inflammation associated with eczema. The term eczema is applied to a wide range of skin conditions with a variety of aetiologies. In general, eczema is characterised by inflammation of the epidermis. Common symptoms associated with eczema include dryness, recurring skin rashes, redness, skin edema (swelling), itching, dryness, crusting, flaking, blistering, cracking, oozing, and bleeding. Eczema includes atopic eczema (atopic dermatitis), contact dermatitis, xerotic eczema, seborrhoeic dermatitis, dyshydrosis, discoid eczema, venous eczema, dermatitis herpetiformus, neurodermatitis and autoeczematisation. Eczema is typically atopic eczema or contact dermatitis.

Atopic eczema is primarily aggravated by contact with or intake of allergens, which include animal hair and dander, food allergens, for example nuts or shellfish, and drugs, for example penicillin.

Contact dermatitis includes allergic contact dermatitis, irritant contact dermatitis and photocontact dermatitis. Photocontact dermatitis includes phototoxic contact dermatitis and photoallergic contact dermatitis.

The skin inflammation may be skin inflammation caused by exposure of the skin to electromagnetic radiation. This includes, for example, exposure to sunlight, heat, X-rays or radioactive materials. Thus, the medicament may be used, or for use, to treat sunburn.

Electromagnetic radiation includes radio waves, microwaves, terahertz radiation, infrared radiation, visible light, ultraviolet radiation, X-rays and gamma rays. Electromagnetic radiation is preferably infrared radiation, visible light, ultraviolet radiation, X-rays and gamma rays, more preferably ultraviolet radiation, X-rays and gamma rays.

Autoimmune diseases can involve an autoimmune response against the skin. Examples of such autoimmune diseases are lupus and psoriasis.

Uremic pruritis is a disorder of the skin associated with chronic renal failure. It also frequently affects patients undergoing dialysis treatment.

Optionally the microbial oil, lower alcohol ester composition or free fatty acid composition herein is used, or is for use, co-administered with a corticosteroid or other therapeutic agent for any of the above medical uses.

In other aspects of the invention, the inflammatory disease may be at least one from a group consisting of atopic dermatitis, allergic contact dermatitis (ACD), irritant contact dermatitis (ICD), photocontact dermatitis, systemic contact dermatitis, rheumatism, psoriasis, lupus and the like.

It will be understood that a medicament for treatment of inflammatory/allergic disease is a medicament which is to suppress or relieve one or more symptoms when the symptom(s) is/are found or suspected to be due to inflammatory/allergic disease. On the other hand, a medicament for prevention of inflammatory/allergic disease is a medicament to suppress an occurrence of one or more symptoms, which may be predicted or anticipated due to inflammatory/allergic disease, typically by pre-administration. However, the terms "medicament for treatment" and "medicament for prevention" should be understood taking into account multiple or general aspects such as the timing of use and/or the symptom(s) to be treated/prevented on use, in line with clinical practice, and should not be restrictively applied.

EXAMPLES

The present invention is described below in detail using working examples. However, the present invention is not limited by these working examples. Unless indicated otherwise, "%" in the working examples below means "% by weight".

Example 1

Effect of Various Types of Δ5 Desaturase Inhibitor on Fatty Acids Produced by Microbial Mass: 1

Five plate culture media, namely Plate Culture Medium A containing no added Δ5 desaturase inhibitor, Plate Culture Medium B to which was added 0.005% by weight sesamin, Plate Culture Medium C to which was added 0.01% by weight sesamin, Plate Culture Medium D to which was added 0.02% by weight sesamin, and Plate Culture Medium E to which were added 0.01% by weight sesamin and 0.01% by weight 2-amino-N-(3-chlorophenyl)benzamide, were prepared according to the product instructions for Potato Dextrose Agar Culture Medium (commercial product name;

Nissui Pharmaceutical Co., Ltd.), excepting the addition or non-addition of the mentioned Δ5 desaturase inhibitor(s) to the potato dextrose agar medium so as to obtain the listed concentration. The size of each plate culture medium was the same, i.e. 90 mm diameter and 5 mm thickness.

Each of Plate Culture Media A to E was inoculated using 100 μL each of a spore suspension of SAM 1860, the mutant strain of Mortierella alpina, and static culturing was performed at 28° C. for 7 days.

After completion of culturing, each plate culture medium with its microbial mass was cut into roughly 1 cm sample wedges, and the sample wedges were transferred to flasks. Then 50 mL of hexane was added per each flat plate, and the mixture obtained was homogenized for 2 minutes to obtain an organic solvent mixed liquid. The organic solvent mixed liquid was centrifuged (2,000 rpm, 810 G), and the supernatant layer of hexane was recovered. Then solvent was removed by distillation to obtain about 40 mg per single plate culture medium of Microbial Oils A to E.

To 0.5 mg of each of the respective Microbial Oils A to E was added 0.10 mL of 10% (v/v) sulfuric acid ethanol solution, and ethyl esterification was performed by reaction for 30 minutes at 80° C. In order to neutralize the reaction solution, 0.18 mL of 1.0 M sodium hydroxide ethanol solution was added, then 0.05 mL of hexane and 0.30 mL of saturated sodium chloride solution were added and extraction was performed, whereby respective Fatty Acid Ethyl Esters A to E were obtained. The fatty acid compositions (%) in Fatty Acid Ethyl Ester compositions A to E were analyzed using gas chromatography. The analytical conditions used for gas chromatography are shown below. The results of gas chromatography are shown in Table 1. Furthermore, the fatty acid composition (%) is the area ratio based on the gas chromatogram.

Gas Chromatography Analysis Conditions
Equipment type: Agilent 6850 GC system (Agilent Technologies, Inc.)
Column: DB-WAX (Agilent Technologies, 30 m×0.25 mm ID, 0.25 μm film thickness) J&W122-7032
Column oven: 180° C.-3° C./min-230° C. (25 min)
Injection temperature: 270° C.
Injection method: split
Split ratio: 20:1
Detector temperature: 270° C.
Detector: FID
Carrier gas: helium (1.0 mL/min, constant flow)

TABLE 1

| Fatty acid composition | Fatty Acid Ethyl Ester A | Fatty Acid Ethyl Ester B | Fatty Acid Ethyl Ester C | Fatty Acid Ethyl Ester D | Fatty Acid Ethyl Ester E |
|---|---|---|---|---|---|
| Palmitic acid | 9.552 | 10.672 | 10.454 | 14.662 | 11.394 |
| Oleic acid | 14.563 | 26.665 | 27.744 | 25.172 | 31.450 |
| DGLA | 31.975 | 22.831 | 23.083 | 18.115 | 18.699 |
| ARA | 5.164 | 2.016 | 1.908 | 1.552 | 0.911 |
| Other | balance | balance | balance | balance | balance |
| DGLA/ARA | 6 | 11 | 12 | 12 | 21 |

As shown in Table 1, for Fatty Acid Ethyl Ester E, which used the microbial Oil E as the raw material, the DGLA/ARA ratio was substantially greater than 13, and this ratio was higher than any of Microbial Oil A, Microbial Oil B, Microbial Oil C, and Microbial Oil D obtained by culturing of the publicly known SAM 1860 strain in the presence of one type of Δ5 desaturase inhibitor. Furthermore, 33.8 mg of fatty acid ester E was obtained from Microbial Oil E.

Example 2

Effect of Various Types of Δ5 Desaturase Inhibitor on Fatty Acids Produced by Microbial Mass: 2

In a corrugated Erlenmeyer flask of 500 mL total volume, 100 mL of a culture medium (pH 6.0) including 2% of glucose and 1% of yeast extract was added, and then 4 types of liquid culture media were prepared, namely, Liquid Culture Medium F with no added Δ5 desaturase inhibitor, Liquid Culture Medium G with 10 mg of sesamin added, Liquid Culture Medium H with 10 mg of 2-amino-N-(3-chlorophenyl) benzamide added, and Liquid Culture Medium I with both 10 mg of sesamin and 10 mg of 2-amino-N-(3-chlorophenyl) benzamide added. An I-26 Stackable Shaker (manufactured by New Brunswick Scientific) was used as the shaking culturing equipment.

After 15 minutes of sterilization of the Liquid Culture Media F to I at 121° C., 1 mL of the pre-cultured liquid culture medium of SAM 1860, mutant strain of Mortierella alpina, was inoculated into the respective liquid culture media and culturing with shaking was performed for 15 days at a rotation rate of 200 rpm and 28° C. temperature. On the 5th day and 10th day, 10 mg of sterilized sesamin was added to Liquid Culture Medium G, 10 mg of sterilized 2-amino-N-(3-chlorophenyl)benzamide was added to Liquid Culture Medium H, and a combination of 50 mg of sterilized sesamin and 10 mg of 2-amino-N-(3-chlorophenyl)benzamide was added to Liquid Culture Medium I. After culturing the microbial mass was recovered by centrifugal separation. After washing with water sufficiently, the microbial mass was freeze dried. 3.2 g of dried microbial mass (Dried Microbial Mass F) was obtained from Liquid Culture Medium F. 2.5 g of dried microbial mass (Dried Microbial Mass G) was obtained from Liquid Culture Medium G. 0.6 g of dried microbial mass (Dried Microbial Mass H) was obtained from Liquid Culture Medium H. 0.6 g of dried microbial mass (Dried Microbial Mass I) was obtained from Liquid Culture Medium I.

175 mL of hexane was added to each of Microbial Masses F to I to extract lipids, with stirring for 30 minutes at room temperature, and the mixture obtained was then filtered to obtain the extract liquid and microbial cells. This operation was repeated 3 times to obtain a hexane extract liquid. The hexane extract liquid was concentrated using a rotary evaporator under reduced pressure. 613.2 mg of microbial oil, Microbial Oil F, was obtained from Dried Microbial Mass F. 328.3 mg of microbial oil, Microbial Oil G, was obtained from Dried Microbial Mass G. 77.7 mg of microbial oil, Microbial Oil H, was obtained from Dried Microbial Mass H. 105.3 mg of microbial oil, Microbial Oil I, was obtained from Dried Microbial Mass I.

To 0.5 mg of each respective microbial oil among Microbial Oils F to I, 0.10 mL of 10% (v/v) sulfuric acid ethanol solution was added, and reaction was conducted for 30 minutes at 80° C. for ethyl esterification. 0.18 mL of 1.0 M sodium hydroxide ethanol solution was added to the liquid after the reaction for neutralization. Then 0.05 mL of hexane and 0.30 mL of saturated sodium chloride solution were added for extraction. 533.2 mg of fatty acid ethyl ester, Fatty Acid Ethyl Ester F, was obtained from Microbial Oil F. 285.4 mg of fatty acid ethyl ester, Fatty Acid Ethyl Ester G, was obtained from Microbial Oil G. 67.6 mg of fatty acid ethyl ester, Fatty Acid Ethyl Ester H, was obtained from the microbial oil H. 91.6 mg of fatty acid ethyl ester, Fatty acid ethyl ester I, was obtained from Microbial Oil I. The fatty acid proportions of the obtained Fatty Acid Ethyl Esters F to I were analyzed by gas chromatography in the same way as in Example 1. The results of the gas chromatography are shown in Table 2. Furthermore, the fatty acid compositions (%) are based on area ratios of gas chromatograms in the aforementioned manner.

The analytical conditions of gas chromatography were similar to those of Example 1.

As shown in Table 2, the DGLA/ARA ratio for Fatty Acid Ethyl Ester I using Microbial Oil I as the raw material was much greater than 13, and this value was higher than that of any of Microbial Oils F, G, and H, which were produced by culturing the known SAM 1860 strain or by culturing the SAM 1860 strain in the presence of one type of Δ5 desaturase inhibitor.

TABLE 2

| Fatty acid composition (wt. %) | Fatty Acid Ethyl Ester F | Fatty Acid Ethyl Ester G | Fatty Acid Ethyl Ester H | Fatty Acid Ethyl Ester I |
|---|---|---|---|---|
| Palmitic acid | 17.991 | 18.418 | 20.996 | 14.071 |
| Oleic acid | 34.217 | 19.680 | 23.840 | 31.332 |
| DGLA | 7.145 | 24.996 | 4.469 | 0.278 |
| ARA | 2.490 | 3.773 | 1.424 | 0.009 |
| Other | balance | balance | balance | balance |
| DGLA/ARA | 3 | 7 | 3 | 31 |

Example 3

Effect of Various Types of Δ5 Desaturase Inhibitor on Fatty Acids Produced by Microbial mass: 3

A one litre (1 L) jar fermenter equipped with disc turbine type agitator blades in two stages was provided. The positions of the agitator blades in the jar fermenter were adjusted so that the relationships between the positions of the agitator blades and the liquid surface of the liquid culture medium (500 mL) contained were as follows: ratios of "distance from culture vessel bottom to agitator blade of the lower stage": "distance from the agitator of the lower stage to the agitator of the upper stage": "distance from the agitator of the upper stage to the culture liquid surface"=4:7:15.

500 mL of a culture medium (pH 6.0) containing 2% glucose and 1% yeast extract was placed in each of four 1 L jar fermenters and 4 types of liquid culture media were prepared: Liquid Culture Medium J with no added Δ5 desaturase inhibitor, Liquid Culture Medium K with 50 mg of added sesamin, Liquid Culture Medium L with 50 mg of added 2-amino-N-(3-chlorophenyl)benzamide and Liquid Culture Medium M with 50 mg of added sesamin and 50 mg of added 2-amino-N-(3-chlorophenyl)benzamide.

After each of Liquid Culture Media J to M was sterilized for 20 minutes at 120° C., 20 mL of pre-cultured liquid culture medium of a Mortierella alpina strain lacking Δ5 desaturase was inoculated into the respective liquid culture medium, and culturing with aeration and agitation was performed for 12 days under 0.6 v.v.m. aeration and 28° C. temperature. On the 3rd day, 4th day, 5th day, 6th day, 7th day, 10th day and 11th day, 50 mg of sterilized sesamin was added to Liquid Culture Medium K, 50 mg of sterilized 2-amino-N-(3-chlorophenyl)benzamide was added to Liquid Culture Medium L, and a combination of 50 mg of sterilized sesamin and 50 mg of 2-amino-N-(3-chlorophenyl)benzamide was added to Liquid Culture Medium M. After culturing, the microbial mass was recovered by centrifugal separation. After washing with water sufficiently, the microbial mass was freeze dried. 2.9 g of dried microbial mass (Dried Microbial Mass J) was obtained from Liquid Culture Medium J. 2.9 g of dried microbial mass (Dried Microbial Mass K) was obtained from Liquid Culture Medium K. 1.5 g of dried microbial mass (Dried Microbial Mass L) was obtained from Liquid Culture Medium L. 2.9 g of dried microbial mass (Dried Microbial Mass M) was obtained from Liquid Culture Medium M.

175 mL of hexane was added to each of Dried Microbial Masses J to M to extract lipids, with stirring for 30 minutes at room temperature, and the mixture obtained was then filtered to obtain the extract liquid and microbial cells. This operation was repeated 3 times to obtain a hexane extract liquid. The hexane extract liquid was concentrated using a rotary evaporator under reduced pressure. 552.0 mg of microbial oil, Microbial Oil J, was obtained from Dried microbial mass J. 379.5 mg of microbial oil, Microbial Oil K, was obtained from Dried Microbial Mass K. 195.5 mg of microbial oil, Microbial Oil L, was obtained from Dried Microbial Mass L. 552.0 mg of microbial oil, Microbial Oil M, was obtained from Dried Microbial Mass M. The contents and types of lipids in the obtained Microbial Oils J to M were analyzed by the thin-layer chromatography/flame ionization detector (TLC/FID) method (IATROSCAN (a trade name; same below), Mitsubishi Chemical Medience Corp.).

Moreover, 0.10 mL of 10% sulfuric acid ethanol solution was added to 0.5 mg of each respective microbial oil among Microbial Oils J to M, and reaction was conducted for 30 minutes at 80° C. for ethyl esterification. 0.18 mL of 1.0 M sodium hydroxide ethanol solution was added to the liquid after the reaction for neutralization. Then 0.05 mL of hexane and 0.30 mL of saturated sodium chloride solution were added for extraction. 480.0 mg of fatty acid ethyl ester, Fatty Acid Ethyl Ester J, was obtained from Microbial Oil J. 330.0 mg of fatty acid ethyl ester, Fatty Acid Ethyl Ester K, was obtained from Microbial Oil K. 170.0 mg of fatty acid ethyl ester, Fatty Acid Ethyl Ester L, was obtained from Microbial Oil L. 480.0 mg of fatty acid ethyl ester, Fatty Acid Ethyl Ester M, was obtained from Microbial Oil M. The contents and types of the fatty acids in Fatty Acid Ethyl Esters J to M obtained were analyzed by gas chromatography.

Results from use of the IATROSCAN and gas chromatography are shown in Table 3.

The IATROSCAN analytical conditions and gas chromatography analytical conditions are listed below.
IATROSCAN Analytical Conditions
Developing solvent:
  0-3 min. $CHCl_3$ : MeOH=95:5 (v/v)
  3-23 min. hexane:diethyl ether:formic acid=90:10:0.2 (v/v)
Sample concentration: 10 mg/mL
Added amount: 5 μL
Gas Chromatography Analysis Conditions
Equipment type: Agilent 7890 GC system (Agilent Technologies)

Column: DB-WAX (Agilent Technologies, 30 m×0.25 mm ID, 0.25 μm film thickness) J&W122-7032
Column oven: 180° C.-3° C./min-230° C. (25 min)
Injection temperature: 270° C.
Injection method: split
Split ratio: 20:1
Detector temperature: 270° C.
Detector: FID
Carrier gas: helium (1.0 mL/min, constant flow)

As made clear by Table 3, when the Δ5 desaturase-deficient strain belonging to *Mortierella alpina* used in the present working example was cultured by itself (Microbial Oil J), when culturing was performed in the presence of one type of Δ5 desaturase inhibitor (Microbial Oil K and Microbial Oil L), and when culturing was performed in the presence of two types of Δ5 desaturase inhibitors (Microbial Oil M), the DGLA/ARA ratio for each oil was greater than or equal to 15.

Among these microbial oils, while Microbial Oil L, to which had been added only a single type of Δ5 desaturase inhibitor, had a reduced total fat content in the liquid culture medium; an unexpected result was also obtained in that the reduction of the total fat content in the liquid culture medium was suppressed for Microbial Oil M, for which two types of Δ5 desaturase inhibitors were used.

TABLE 3

|  | Microbial Oil J | Microbial Oil K | Microbial Oil L | Microbial Oil M |
|---|---|---|---|---|
| Triglyceride | 457.6 | 305.8 | 153.6 | 442.2 |
| Diglyceride | 27.7 | 1.6 | 12.4 | 35.2 |
| Monoglyceride | 6.3 | 6.0 | 12.6 | 14.0 |
| Phospholipid | 0.2 | 0.2 | 0.1 | 0.8 |
| Free fatty acid | 0.0 | 1.3 | 0.5 | 0.0 |
| Sterol | 50.0 | 40.3 | 14.7 | 55.5 |
| Other | 10.1 | 24.4 | 1.6 | 4.3 |
| Total Lipids | 552.0 | 379.5 | 195.5 | 552.0 |
| Palmitic acid | 66.3 | 48.3 | 25.1 | 88.0 |
| Oleic acid | 60.1 | 63.0 | 37.4 | 90.2 |
| DGLA | 181.2 | 100.0 | 27.9 | 141.8 |
| ARA | 5.18 | 0.58 | 0.45 | 0.05 |
| DGLA/ARA | 35 | 172 | 62 | 2836 |
| Total fatty acid (value calculated from total lipids) | 480.0 | 330.0 | 170.0 | 480.0 |
| Dried microbial | 2880.5 | 2889.7 | 1509.9 | 2871.2 |

* The values for each or the fatty acids were calculated based on the total fatty acid esters (mg).
* Except for DGLA/ARA, the values refer to the amount produced (mg) per 500 mL of culture medium.

Example 4

(1) Refining of the Fatty Acid Ethyl Ester by Rectification

Each of Fatty Acid Ethyl Ester compositions J, K, and M obtained in Example 3 was subjected to a rectification process under reduced pressure, to obtain respective fractions (Fatty Acid Ethyl Ester Fractions J, K and M) each of which contains the Fatty Acid Ethyl Esters J, K, or M as main component, derived from fatty acids having 20 or more carbons.

The results are shown in Table 4. As made clear by Table 4, by rectification of the ethyl ester having the DGLA/ARA ratio controlled at 2836 by addition of sesamin and 2-amino-N-(3-chlorophenyl)benzamide in the working examples, a fatty acid ester fraction was obtained that had greater than or equal to 20 carbon atoms and extremely low ARA content.

TABLE 4

| Fatty acid composition (wt %) | Fatty Acid Ethyl Ester J | Fatty Acid Ethyl Ester K | Fatty Acid Ethyl Ester M |
|---|---|---|---|
| DGLA | 61.80 | 59.53 | 65.06 |
| ARA | 1.78 | 0.50 | 0.03 |
| DGLA/ARA | 35 | 120 | 2024 |

(2) Refining of Fatty Acid Ethyl Esters Using Column Chromatography

Fatty Acid Ethyl Esters J, K, and M after rectification, which had the compositions shown in Table 4, were subjected to further high purification using ODS (Octa Decyl Silyl)-HPLC. The separation conditions are listed below.
Separation Conditions
Column: ODS AQ S-5012 nm (YMC Corp., Ltd.), 20φ×300 mm
Separation liquid: methanol
Flow rate: 25 mL/min
Column temperature: 40° C.
Sample load: 1.42 g
Detectors: UV/Vis spectrophotometer and differential refractometer Table 5 shows the fatty acid compositions after ODS-HPLC purification of each fatty acid ethyl ester fraction when the HPLC yield was 65%. Furthermore, the fatty acid compositions (%) are based on area ratios of gas chromatograms in the aforementioned manner.

TABLE 5

| Fatty Acid Composition (%) | Fatty Acid Ethyl Ester Fraction J | Fatty Acid Ethyl Ester Fraction K | Fatty Acid Ethyl Ester Fraction M |
|---|---|---|---|
| DGLA | 94.72 | 94.12 | 95.89 |
| ARA | 1.53 | 0.78 | 0.05 |
| 20:4 n-3 | 1.15 | 0.10 | 0.07 |
| DGLA/ARA | 62 | 121 | 1918 |

As made clear by Table 5, for each of the fatty acid ethyl ester fractions (J, K, and M) ODS-HPLC refining was able to increase the content of DGLA. In particular, it was possible to attain a purity of 95% by weight or greater particularly for Fatty Acid Ethyl Ester Fraction M.

On the other hand, there was no great change in the DGLA/ARA ratios for the fatty acid ethyl ester fractions obtained by further high purification of DGLA in comparison to the DGLA/ARA ratios of the crude oils prior to refining. It is understood that separation of DGLA from ARA in a refining process is difficult. In order to obtain a high concentration of DGLA ethyl ester with a low content of ARA, it is therefore understood that it is effective to increase the DGLA/ARA ratio beforehand, at an early stage.

In particular, it is understood that culturing a microbe strain while adding two types of Δ5 desaturase inhibitors in combination (e.g. sesamin and 2-amino-N-(3-chlorophenyl) benzamide) during growth of the microbe is effective for this.

It is therefore understood that the present invention provides a microbe and microbial oil including an oil having a high DGLA/ARA ratio, and also provides lower alcohol esters and free fatty acids obtained from such microbes and oils.

INDUSTRIAL APPLICABILITY

The DGLA-containing microbial oil of the present invention has a low content of arachidonic acid. Thus, while administering a given amount of DGLA, the effect of arachidonic acid can be made small. A composition can be provided that is suitable for applications for which arachidonic acid is undesirable, e.g. as anti-allergic agents and as anti-inflammatory agents.

The invention claimed is:

1. A microbial oil recovered from a cultured microbial biomass wherein said microbial oil comprises dihomo-γ-linolenic acid as a constituent fatty acid of the oil, the microbial oil having a weight ratio of arachidonic acid (ARA) relative to dihomo-γ-linolenic acid (DGLA) ARA: DGLA) of less than 1/20, wherein said microbial oil is obtained from a microbe grown in a culture medium containing a Δ5 desaturase inhibitor, or is obtained from a microbe that is mutated to have a reduced or lost Δ5 desaturase enzyme activity, or is obtained from the microbe that is mutated to have a reduced or lost Δ5 desaturase enzyme activity that is cultured in the presence of a Δ5 desaturase inhibitor.

2. The microbial oil according to claim 1, wherein said weight ratio is less than or equal to 1/30.

3. The microbial oil according to claim 1, wherein the microbial oil has a triglyceride content of greater than or equal to 70% by weight.

4. The microbial oil according to claim 3 having a triglyceride content of greater than or equal to 90% by weight.

5. The microbial oil according claim 3, wherein the microbial oil is a crude oil, and wherein the triglyceride content is greater than or equal to 90% by weight and said weight ratio of arachidonic acid relative to dihomo-γ-linolenic acid is less than or equal to 1/20.

6. The microbial oil according to claim 3, wherein the microbial oil is a refined oil, wherein the triglyceride content is greater than or equal to 90% by weight and said weight ratio of arachidonic acid relative to dihomo-γ-linotenic acid is less than or equal to 1/30.

7. The microbial oil according to claim 1, containing phospholipid at from 0.1 to 10% by weight.

8. The microbial oil according to claim 1, wherein the microbial oil has a saturated fatty acid content of less than or equal to 40% by weight.

9. A lower alcohol ester composition comprising dihomo-γ-linolenic acid ester, or a free fatty acid composition comprising dihomo-γ-linolenic acid, in which a weight ratio of arachidonic acid relative to dihomo-γ-linolenic acid (arachidonic acid/dihomo-γ-linolenic acid) is less than 1/20. produced or obtainable by a method comprising subjecting a microbial oil according to claim 1 to an ester exchange reaction or hydrolysis reaction.

10. The lower alcohol ester composition or the free fatty acid composition according to claim 9, wherein the arachidonic acid content is less than or equal to 7% by weight.

11. The lower alcohol ester composition or the free fatty acid composition according to claim 9, wherein the composition is foodstuffs, dietary supplements, medicaments, cosmetics, or animal feed.

12. The microbial oil according to claim 1, wherein the arachidonic acid content is less than or equal to 7% by weight.

13. The microbial oil according to claim 1, wherein the composition is foodstuffs, dietary supplements, medicaments, cosmetics, or animal feed.

14. A microbial biomass containing the microbial oil according to claim 1.

15. A liquid culture medium containing the microbial biomass according to claim 14.

16. The liquid culture medium according to claim 15, wherein a content of the microbial biomass is greater than or equal to 2.5 g/L, in terms of dry weight of the microbial biomass.

17. The liquid culture medium according to claim 15, wherein the liquid culture medium contains the microbial oil at a content of 0.4 g/L or greater.

18. A lower alcohol ester composition derived from a microbial oil and comprising dihomo-γ-linolenic acid ester, or a free fatty acid composition derived from a microbial oil and comprising dihomo-γ-linolenic acid, in which a weight ratio of arachidonic acid relative to dihomo-γ-linolenic acid (arachidonic acid/dihomo-γ-linolenic acid) is less than 1/20 wherein said microbial oil is obtained from a microbe grown in a culture medium containing a Δ5 desaturase inhibitor, or is obtained from a microbe that is mutated to have a reduced or lost Δ5 desaturase enzyme activity, or is obtained from the microbe that is mutated to have a reduced or lost Δ5 desaturase enzyme activity that is cultured in the presence of a Δ5 desaturase inhibitor.

19. A method of producing a lower alcohol ester composition or free fatty acid composition according to claim 9, from the microbial oil the method comprising:
 (a) subjecting a microbial oil to an ester exchange reaction or a hydrolysis reaction, to obtain dihomo-γ-linolenic acid ester, or a free fatty acid composition comprising, dihomo-γ-linolenic acid, wherein said microbial oil comprises dihomo-γ-linolenic acid as a constituent fatty acid of the oil, the microbial oil having weight ratio of arachidonic acid relative to dihomo-γ-linolenic acid (arachidonic acid/dihomo-γ-linolenic acid) of less than 1/20;
 (b) obtaining a mixture of free fatty acids or lower alcohol esters of fatty acids by hydrolysis or alcoholysis of the microbial oil, and
 (c) rectifying the mixture of free fatty acids or lower alcohol esters to obtain a free fatty acid or lower alcohol ester composition in which the fatty acids have at least 20 carbon atoms.

20. The method of producing a lower alcohol dihomo-γ-linolenic acid ester or free dihomo-γ-linolenic acid comprising producing a lower alcohol ester composition or free fatty acid composition in accordance with according to claim 19, further comprising:
 (d) performing fractionation and purification of the lower alcohol ester of dihomo-γ-linolenic acid or of dihomo-γ-linolenic acid, by reverse phase distribution type column chromatography, from the free fatty acid or lower alcohol ester composition in which the fatty acids have at least 20 carbon atoms.

* * * * *